US006272723B1

(12) United States Patent
Rathjen

(10) Patent No.: US 6,272,723 B1
(45) Date of Patent: Aug. 14, 2001

(54) BIER SYSTEM

(76) Inventor: Fordyce Bernhardt Rathjen, 116 Wallrich Rd., Cecil, WI (US) 54111

( * ) Notice: Subject to any disclaimer, the term of this patent is extended or adjusted under 35 U.S.C. 154(b) by 0 days.

(21) Appl. No.: 09/139,621

(22) Filed: Aug. 25, 1998

(51) Int. Cl.[7] .................. A61B 17/00
(52) U.S. Cl. .................. 27/1
(58) Field of Search .................. 27/1; 119/428

(56) References Cited

U.S. PATENT DOCUMENTS

| | | | |
|---|---|---|---|
| D. 296,249 | 6/1988 | Was | D30/116 |
| D. 340,321 | 10/1993 | Bonn | D30/114 |
| 4,082,384 | 4/1978 | Dold | 312/3 |
| 4,723,512 | 2/1988 | Margolis | 119/15 |
| 5,305,708 | 4/1994 | Keisler, Jr. | 119/17 |
| 5,551,372 | 9/1996 | Nicholls | 119/474 |
| 5,704,103 * | 1/1998 | Crowley et al. | 27/1 |
| 5,794,318 * | 8/1998 | Parker et al. | 27/1 |
| 5,903,961 * | 5/1999 | Parker et al. | 27/1 |

* cited by examiner

*Primary Examiner*—Thomas Price
(74) *Attorney, Agent, or Firm*—Wilhelm Law Service; Thomas D. Wilhelm

(57) ABSTRACT

This invention pertains to assisting individuals in dealing with the death of another by providing a novel bier system designed to provide active and uplifting association with life. The bier system comprises a bier for receiving a representation of the deceased, and an aviary containing live birds, in associative proximity with the bier. The aviary is of sufficient size and openness of interior chamber therein to facilitate significant movement of the birds about at least one interior chamber of the aviary, and to facilitate persons approaching the bier to make an association of activity of the birds with proximity of the bier. The soothing sounds and sights of bird activity assist the bereaved and help them to remember, even as they grieve, that life in general continues.

28 Claims, 10 Drawing Sheets

BIER SYSTEM

FIELD OF THE INVENTION

The present invention is directed toward assisting the bereaved in dealing with the death of another. More particularly, the present invention is a bier system for use inside a building structure.

BACKGROUND OF THE INVENTION

The funeral profession works to ease grief that often accompanies the death of a loved one. Such work has focused upon a variety of tools, including professional sympathy in combination with the use of passive displays, such as flowers, canopies or other types of display assemblies, typically set beside or around the coffin or bier arrangement, to distract the bereaved from their anguish and/or to provide the bereaved with a soothing setting within which to deal with their grief.

Professional sympathy may come across as "professional" but not "genuine." The conventional passive displays are intended to soften the impact of death by providing an attractive and tasteful environment during the activities related to the funeral. However, passive displays have limited ability to touch and heal, or otherwise effectively reach, the human emotion and human spirit of the bereaved.

It is desirable to provide alternative or additional methods of comforting or otherwise assisting the grieving in dealing with their grief. It is further desirable to provide novel methods of lightening the funeral home and/or related environment.

It is accordingly an object of the invention to provide a novel method of comforting bereaved persons, which method will be perceived by the bereaved as both genuine and uplifting.

Another object of the invention is to provide a living display including animal activity and sound perceived by humans as light-hearted sound, for use in a funeral environment.

Still another object of the invention is to provide an aviary for use in a funeral environment.

Yet another object of the invention is to provide a multiple unit aviary which can be assembled in one or more configurations for use in association with a casket or bier.

A further object of the invention is to provide a portable aviary for use with a bier in a funeral home environment.

A still further object is to provide a method of lightening emotions and/or spirits of bereaved persons by specifically providing elements of a light-hearted environment in a funeral home.

SUMMARY OF THE INVENTION

The invention generally comprises a bier system for use inside a building structure. The bier system comprises a bier for receiving a casket thereon, and an aviary. The bier has a first length and a first width.

The aviary comprises an enclosing structure which defines at least one interior chamber for receiving birds therein. The aviary has a second length and a second width. One of the second length and the second width is at least as great as one of the first length and the first width. The aviary is juxtaposed sufficiently close to the bier that a person approaching the bier for viewing of a representation of the deceased typically perceives activity of birds in the aviary in association with the representation of the deceased.

In preferred embodiments, the aviary defines a recess in the outer perimeter, outside the enclosing aviary structure, and at least a portion of the bier disposed in the recess.

Preferably, the aviary is of sufficiently small size and weight that the aviary is substantially portable within a building.

In preferred embodiments, at least one interior chamber in the enclosing structure defines a volume of at least 50 cubic feet, more preferably at least 65 cubic feet, still more preferably at least 100 cubic feet.

In some embodiments, the bier system further comprises a left section and optionally a right section, at left and right respective sides of the bier system, the left section having a first interior chamber and the right section, when used, having a second interior chamber. Preferably, the left and right sections are disposed at opposing ends of the bier system and at opposing locations on a rear wall of the bier system.

In some embodiments, the bier system comprises an opening between first and second interior chambers, whereby the first and second interior chambers define a unitary composite interior chamber, such that birds can fly through the opening between the first and the second interior chambers.

Preferably, the bier system further comprises an opening between a third rear interior chamber and the first interior chamber, and optionally between the third interior chamber and the second interior chamber, whereby the combination of the first, second, and third interior chambers defines a unitary composite interior chamber, such that a bird can fly through the first and second openings, and thus among all of the first, second, and third interior chambers.

In the multiple chamber embodiments, it is preferable that each of the chambers defines a volume of at least 50 cubic feet, more preferably at least 65 cubic feet, and still more preferably at least 100 cubic feet.

The invention is also embodied in a method of providing comfort to bereaved persons who are associating with a representation of a deceased. The method comprises associating an aviary and a bier for receiving a casket thereon. The bier has a first length and a first width. The aviary comprises an enclosing structure defining a chamber having at least one live bird therein. The aviary has a second length and a second width. One of the second length and the second width is about at least as great as one of the first length and the first width. The aviary is juxtaposed sufficiently close to the representation of the deceased that a person approaching the representation of the deceased for viewing of the representation of the deceased can, and typically does perceive activity of the at least one bird in the aviary in association with the representation of the deceased.

Preferably, the method of providing comfort to a bereaved person includes making the association with the aviary, and thus the birds, in a building. Except for the viewing system being typically located inside a building, the building is not a significant element of the bier system.

By virtue of the portability of the aviary, and separately the conventional portability of the bier, the bier system of the invention can be moved from building to building, albeit with the assistance of equipment such as is commonly used to move furniture.

Figure 1:
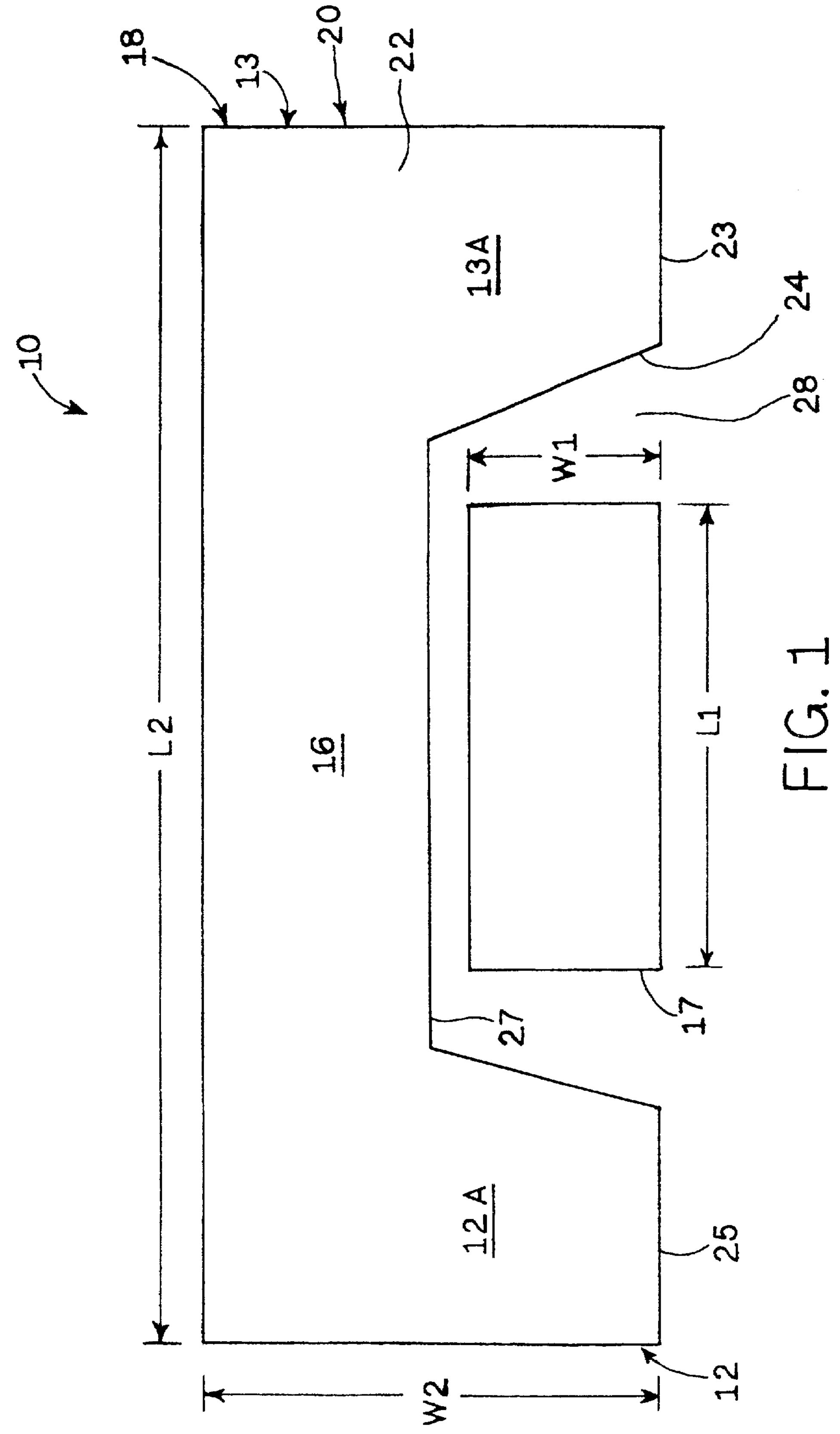
FIG. 1 is a representative top view of a bier system of the invention.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

The following detailed description of the illustrated embodiments is made in the context of a bier system for use inside a building structure, wherein the building structure is not a significant element of the bier system. Preferred building structures include funeral homes, mausoleums, churches, and other buildings used for funeral or funeral-related services. The bier systems of the invention can also readily be used in the open air, not in a building.

The invention, as illustrated in FIG. 1, is a bier system or assembly 10 having a left side 12 and a right side 13. Bier system 10 comprises a bier 17 juxtaposed proximate an aviary 18. Bier system 10 is typically, but not necessarily, used inside a building wherein a typical use of the building is conducting funeral activities.

The bier is typically used for receiving a casket thereon, and has a length "L1" and a width "W1". Biers are well known in the art and usually comprise structure for supporting caskets for funeral activities. Variations of the bier, also known in the art as a church cart, include collapsible casket-receiving structures such as a showroom truck or a casket truck.

As used herein, "bier" 17 includes any underlying support intended to support a representation of the deceased. Thus, in addition to casket-receiving structures, "bier" 17 includes tables and other support structures for receiving e.g. a casket, a vase of ashes of the deceased, and the like, and need not correspond closely to the length and width dimensions recited herein, but should support the representation of the deceased at a comfortable height for viewing, such as about 24 inches to about 42 inches above the floor or ground.

Aviary 18 is generally defined by an enclosing structure 20 which, when in use, encloses a unitary composite interior chamber or inner space 22 for holding birds, such as small finches. The aviary has a length "L2" and a width "W2". The length and/or the width of the aviary is at least as great as either the length or width of the bier and the height is typically, though not necessarily, at least as great as the height of an adult person. Thus, at least one of "L2" and "W2" is at least 5 feet long, preferably at least 6 feet long, and may be 7 feet or 8 feet, or more.

As illustrated in FIG. 1, the aviary has a left section 12A corresponding with left side 12, and having a left front edge 25; and a right section 13A corresponding with right side 13, and having a right front edge 23. A rear section 16 is located between left and right sections 12A, 13A and has a front edge 27 disposed rearwardly of the front edges of the left and right sections thereby defining a recess 28 in the front portion of the perimeter of the aviary between front edge 27 of the rear section and front edges 23, 25 of the right and left front sections 13A, 12A, respectively.

Aviary 18 is located in close proximity to the bier such that the bereaved at e.g. a wake or funeral, while viewing representation of the deceased on the bier, readily perceive activity of any birds located in the aviary.

Figure 2:
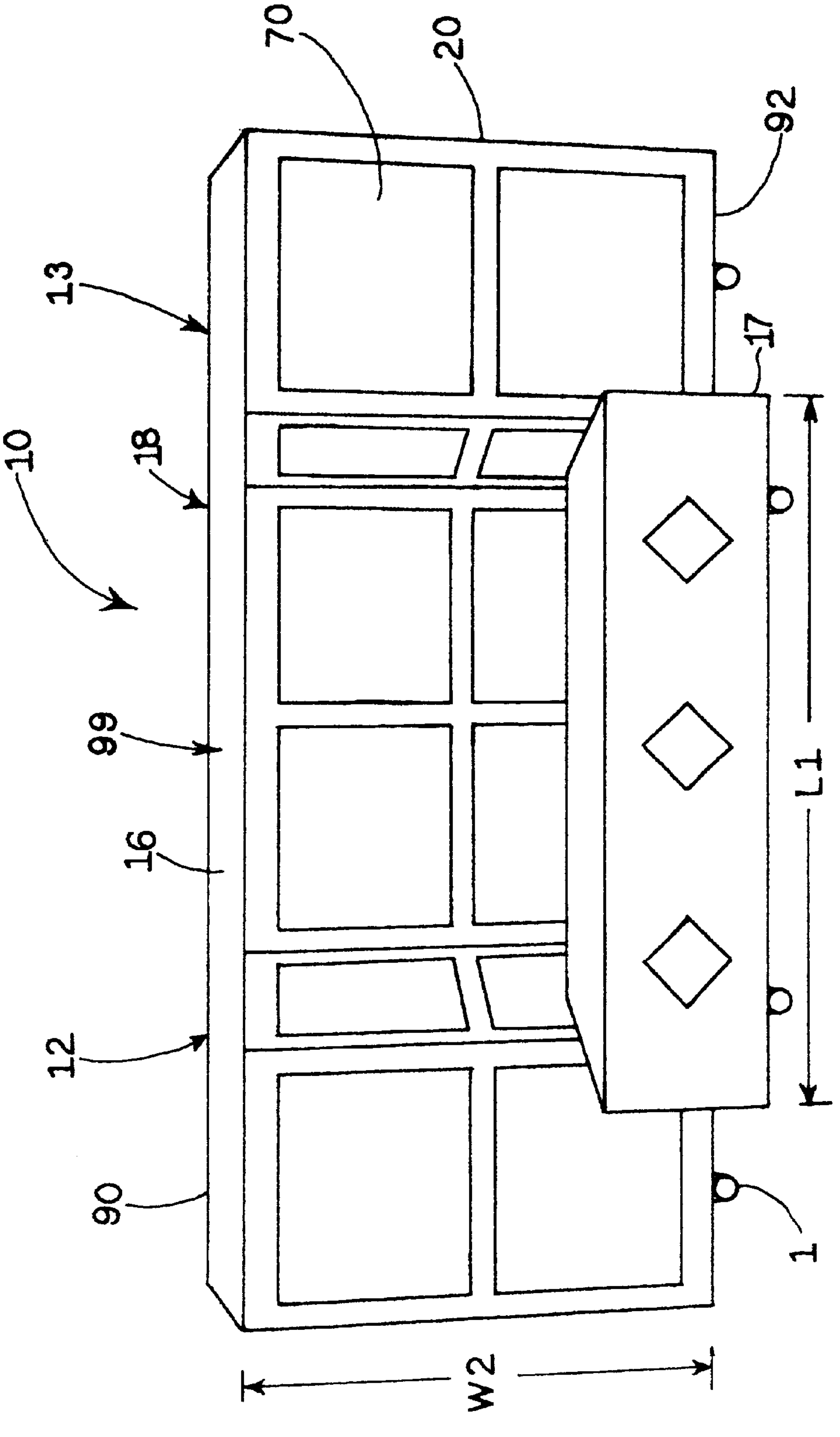
FIG. 2 is a representative front elevation view of the bier system of FIG. 1 with the front of the bier forward of the front edges of the side units of the aviary.
Figure 3:
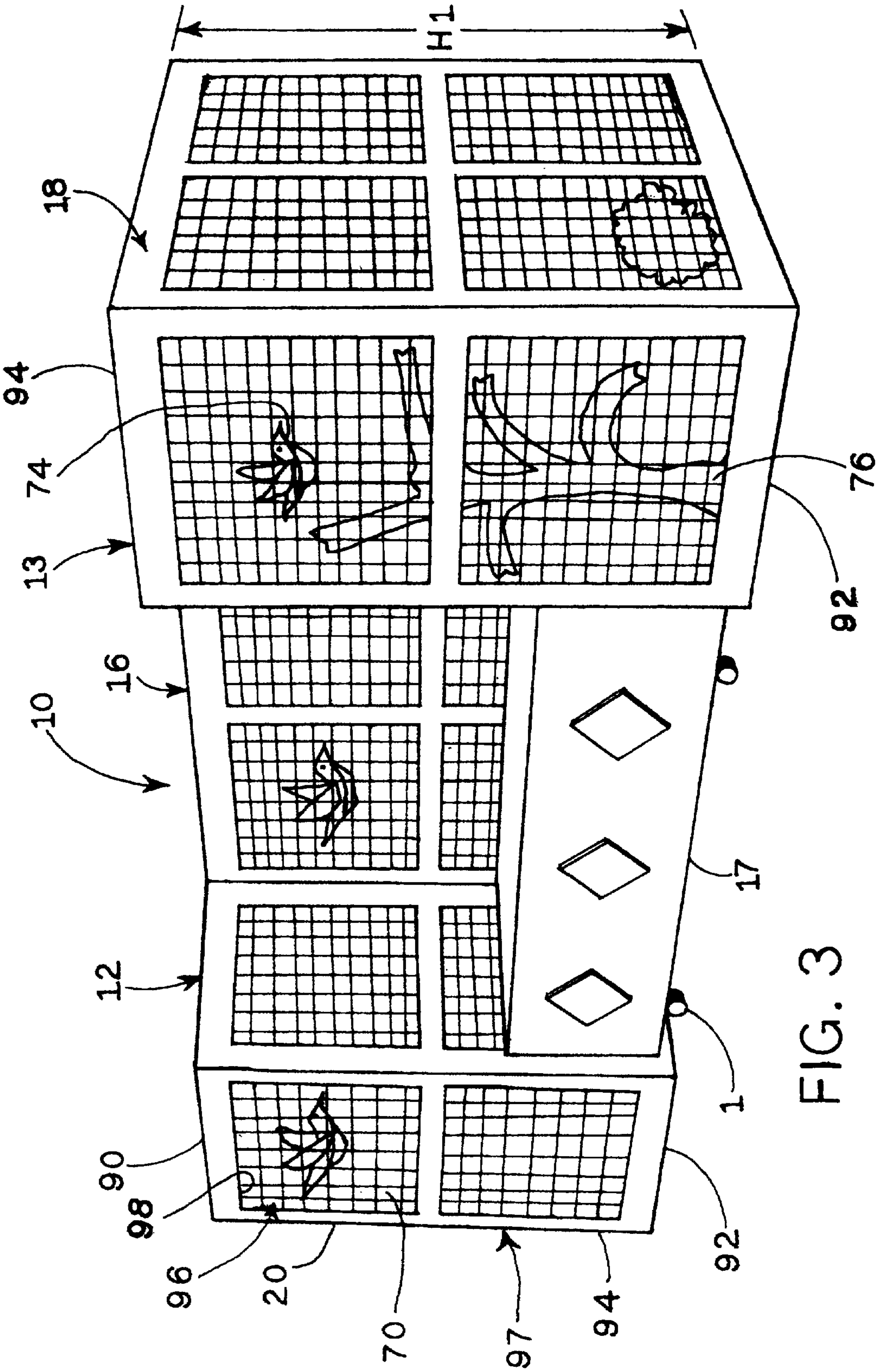
FIG. 3 is a representative right front pictorial view of the bier system of FIG. 1, showing birds and bird support structure therein.

Referring to the embodiment represented by FIGS. 1–3, aviary 18 defines a closed outer perimeter 24. A recess 28 in the outer perimeter receives bier 17. Namely, the bier is located within the recess and outside the enclosing structure. Typically, a portion, if not all, of the bier is located within the recess. However, the bier can be located outside recess 28 so long as there remains a definite association between the activity of birds in the aviary with the proximity of the bier.

The bier system is described herein as being "portable." Church carts and the like used as bier 17 are conventionally available, and are conventionally portable as wheeled elements, and can be transported in station wagons and like-sized vehicles.

Aviaries or aviary units of the invention are typically larger in volume overall than a typical bier, but are smaller than a typical USA funeral home building. Thus, the aviary units are sized more like large pieces of furniture, and one may use a small truck, such as a pick-up truck or a 2–5 Ton flat bed truck for transport of such aviary units of the invention.

Indeed, aviary units of the invention typically have the appearance of furniture, thus being made with high quality wood and like materials, having a typical furniture-like finish, as a frame. The frame defines large-size openings 70 in the front and/or side walls, and wire 72 is used across the openings, thereby to define large open, wire-protected, apertures through which the activities of the birds 74 can be sensed and perceived, but which prevent the birds from leaving the aviary. See FIGS. 2 and 3. Inside the aviary units are various bird-friendly structures such as perches, live and/or artificial foliage 76, feeders, waterers, nests, and the like. In addition, aesthetically pleasing objects can also be placed inside the aviary units e.g. for decorative purposes.

The aviary overall is sufficiently small in size and weight that the assembly, or subassemblies defining side or rear units, are substantially portable within the building, or from building-to-building. Namely, the bier system of the present invention can be carried or conveniently transported from one location to another by ordinary furniture moving equipment and tools, or as illustrated in FIG. 2, the aviary, aviary units, and/or the bier can be supported on a wheeled dolly mechanism such as a truck 1 or other such similar transport device to facilitate portability. Such transport devices are generally suitable for moving loads within buildings and from building-to-building, but are generally not suitable as road transport vehicles.

Typically, the overall volume of the aviary defined inside the frame, and thus available for use by birds, is at least 50 cubic feet. Preferred volume of at least 65 cubic feet gives the birds more exercise area, and potentially more visibility to the bereaved and/or other attendees to funeral activities. Some embodiments employ 100 cubic feet or more of interior space inside the framework of an aviary unit. Where multiple sections 12A, 13A, and 16, are used, each section desirably comprehends the above-described interior volumes, whereby the overall volume of the multiple sections can be in combination, for example, at least about 100 cubic feet, up to at least about 150 cubic feet, or up to at least about 200 cubic feet, or up to about 300 cubic feet, or more, and all sizes in between. The unitary embodiment of FIG. 1 comprehends similar larger overall size. In general, the overall size of aviary 10 comprehends all sizes up to about 1000 cubic feet. As the size becomes greater than 1000 cubic feet, the ability to move the aviary about within the funeral context can become diminished. While certain embodiments comprehend aviaries up to 25 to 35 percent larger than 1000 cubic feet, such embodiments are not generally preferred because the size obviates the intimacy impression desired to be achieved by use of aviary 10.

The above sizes are illustrative only of typical embodiments contemplated. Other sizes and configurations are possible, and are contemplated by the present invention so long as size does not prohibit the above-described ready portability into or out of commercial buildings having double-wide, 36-inch personnel doors. Thus, the aviary unit of the invention is larger than a typical birdcage, and unlike a birdcage, the aviary unit allows a spacious living environment for the birds. However, the size of the aviary is limited so as to fit the above stated requirements to traverse personal doors, and requirements for furniture-like portability. Accordingly, length “L2” of overall aviary is typically no more than 20 feet, preferably no more than 16 feet, and may be no more than 12 feet; and width “W2” of the overall aviary is typically no more than 8 feet, preferably no more than 6 feet. Where multiple aviary units are used, the combined length and width of any one unit is generally no more than 16 feet, preferably no more than 12 feet.

The aviary is smaller than an aviary building. Namely, the bier system is not a significant element of the structure of the building, if any, within which the aviary is used.

Height H1 of aviary 18 is such that at least some of the bird activity in the aviary can be at eye level, where the bereaved can easily see and hear the activity. Accordingly, the top of the aviary should be typically about 5 feet to about 8 feet, preferably about 6 feet to about 7 feet, above the floor. The bottom of the aviary can reach generally to the floor, or can be higher such that the aviary is supported on e.g. a low table. But the overall height “H1” must be great enough to support significant movements of the birds, especially free flight of the birds. Thus, overall height is at least 3 feet, preferably at least 4 feet so long as other dimensions are sufficiently large to support free flight of the birds. “Free flight” as used herein means flight supported only by wing movement, and not including any leg activity such as is used for launching such free flight.

The aviary units of the invention offer the simulation of a miniature natural environment. For influencing the bereaved, it is important that the birds have significant ability to move about the aviary. Overall potential for bird movement is directly related to the internal volume of the aviary, and is inversely related to size of the birds. The invention contemplates that the internal volume of the aviary be quite accommodating of bird movement, especially when small birds such as finches are used. Accordingly, such small birds are preferred, in combination with a generous-size aviary wherein length “L2” is 12–20 feet, width “W2” is about 3–8 feet, and height “H1” is 5–8 feet.

The aviary can house a lighting system to replicate natural light, and/or a timing system to create day/night simulations. The aviary can include a feeding system including feeding structure, watering system including watering structure, a cleaning system including cleaning structure, bedding system including bedding structure, and/or nesting structure. As indicated above, the aviary can contain various types of foliage and or natural forage such as branches, berries, plants, grasses and/or perching trees to enable the birds to build nests, land, perch, feed young, and the like.

The aviary structure is designed to permit not only the creation of natural habitat, but also to allow perception of such habitat by the bereaved and others attendant associated funeral activities.

The aviary structure incorporates the basic components of a typical aviary, illustrated in FIGS. 2 and 3, including an upper frame member 90 and a lower frame member 92 constructed from framing material such as wood, plastic, metal, or the like in order to simulate a natural feel or habitat. Any structurally suitable material can be used as the framing material. Other frame members include at least one side wall 94, having a first end and a second end. The first end can be adjacent a bottom surface of the upper frame member and the second end can be adjacent a top surface of the lower frame member. The two ends of the side wall can connect the upper frame member to the lower frame member. Similarly, other side walls at the opposing ends, the front, the rear, and about the perimeter of recess 28, further define the free-flight space enclosed within aviary 10.

The upper and lower frame members and the side wall, in combination, form the basic structure of the aviary. The aviary structure has a plurality of outer upstanding surfaces, creating an outer perimeter 97. Mesh wire 96 extends across the several apertures 98 about the outer perimeter created by the frames and the side walls to enclose the entire surface area of the outer perimeter of the aviary. Preferably, mesh wire 96 also closes the aperture 98 at the top 99 of the aviary.

The sizes of the openings in the wire mesh are such as to prevent birds from exiting the aviary while providing for high levels of air flow through the aviary, and providing high levels of sensory perception, e.g. visibility and audibility of the sights and sounds of the birds in the aviary, readily perceived by persons who are in relatively close proximity to the bier system.

Figure 4:
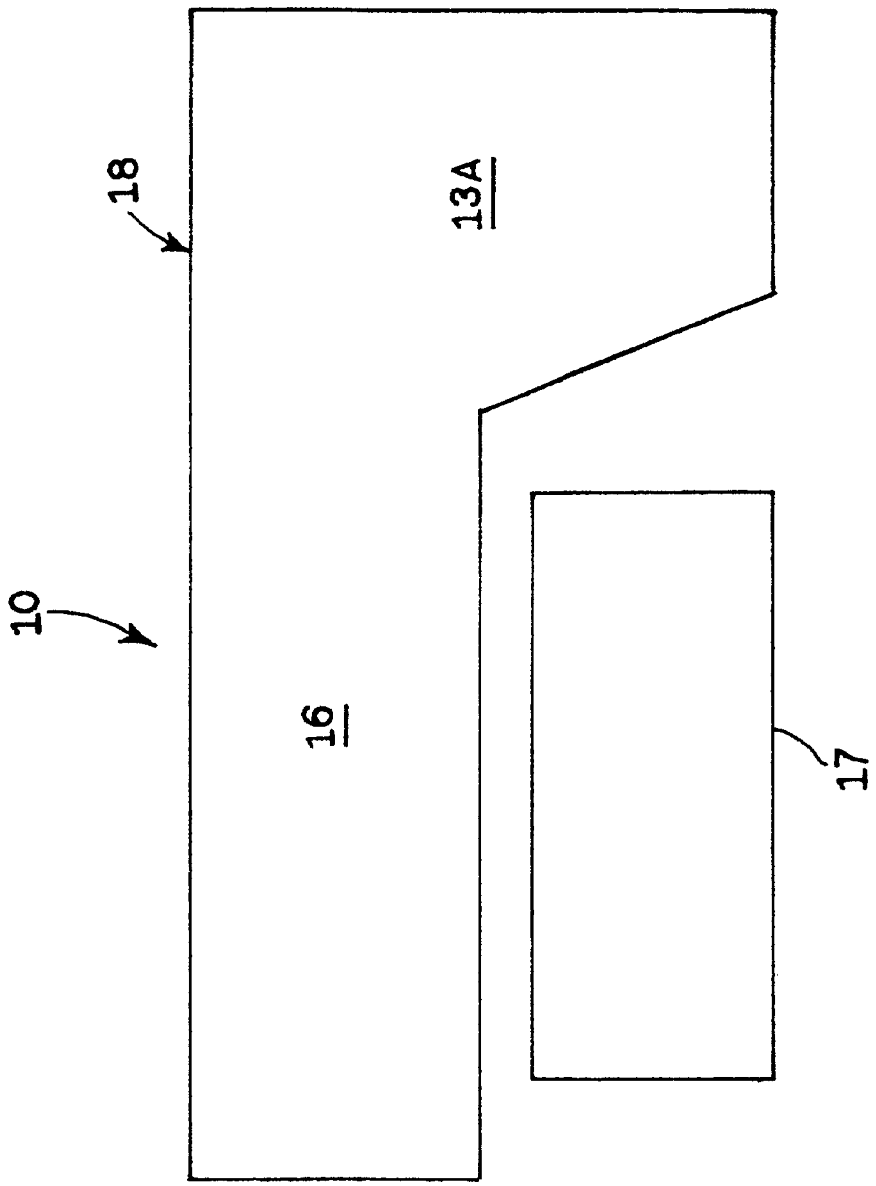
FIG. 4 is a representative top view of a second embodiment of the bier system of FIG. 1.

FIG. 4 illustrates modifications to the first embodiment wherein right section 13A is disposed on the right end of rear section 16. A left section such as 12A of FIG. 1 could as well be used instead of right section 13A. As illustrated, the aviary shown in FIG. 4 borders the bier on two sides.

Figure 5:
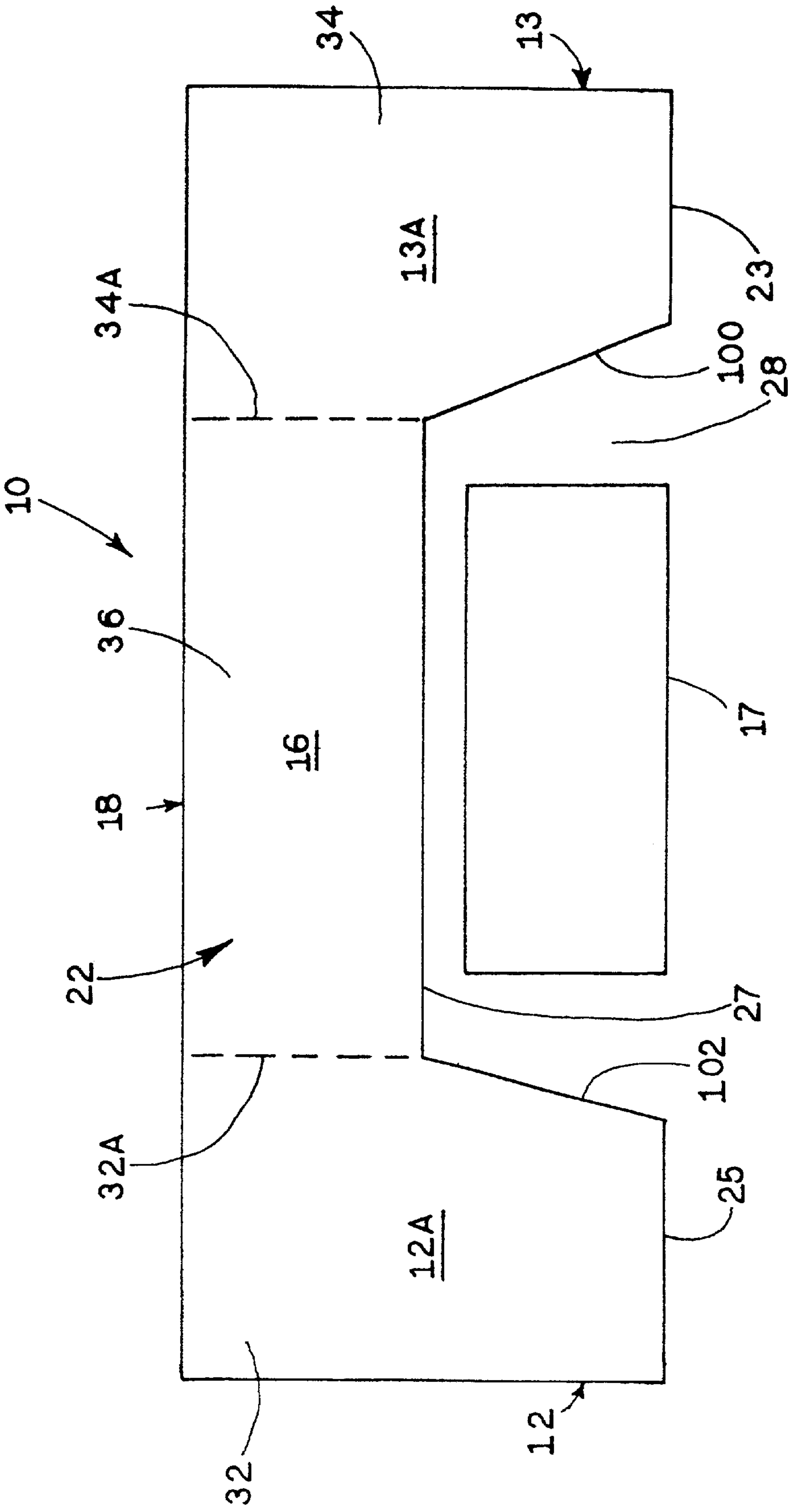
FIG. 5 is a representative top view of a multiple-aviary-unit third embodiment of bier systems of the invention.

FIG. 5 illustrates a three-piece aviary 18 assembled from separately-fabricated aviary units. Aviary 18 of FIG. 5 comprises a left unit defining left section 12A corresponding with left side 12, and having a left front edge 25. A right unit defines right section 13A corresponding with right side 13, and having a right front edge 23. A rear unit defines rear section 16, located between left and right sections 12A, 13A, and has a front edge 27 disposed rearwardly of front edges 23, 25 of the right and left sections, thereby defining recess 28 bounded by front edge 27, left edge 100 of right section 13 and right edge 102 of left section 12.

The sections, in respective order, comprise a first left interior chamber 32, a second right interior chamber 34, and a third central interior chamber 36. The three chambers, in combination, comprise a larger unitary composite generally designated as interior chamber 22. Birds can be located in the larger chamber or in anyone or all three of the smaller interior chambers.

The embodiment of FIG. 5 comprises first and second openings, illustrated by lines 32A, 34A between third central interior chamber 36 and the first and second interior chambers 32, 34, respectively. Openings 32A, 34A between the respective interior chambers 32, 34, 36, in combination with the chambers, define the unitary composite interior chamber 22 such that birds located within the aviary can fly freely through the openings and throughout unitary composite interior chamber 22. However, the sections 12A, 13A, and 16, seen in FIG. 5, can be disassembled and separated into individual respective units, for transportation off site, for movement within the funeral home or any other building structure, or servicing or replacement of one or more of the units.

Openings 32A, 34A can be large or small. In the large dimension, the openings extend the full front-to-rear, and top-to-bottom, dimensions of the respective units at the respective locations of the openings. At the other end of the spectrum, openings 32A, 34A are large enough for a bird to fly into but not through the openings. Birds thus traverse the opening by landing and/or perching on structure at the opening, and moving through the opening from such structure. All opening sizes between such large and small openings are contemplated. Relatively larger openings are preferred, for encouraging free movement and other activity by birds in the aviary.

Figure 6:
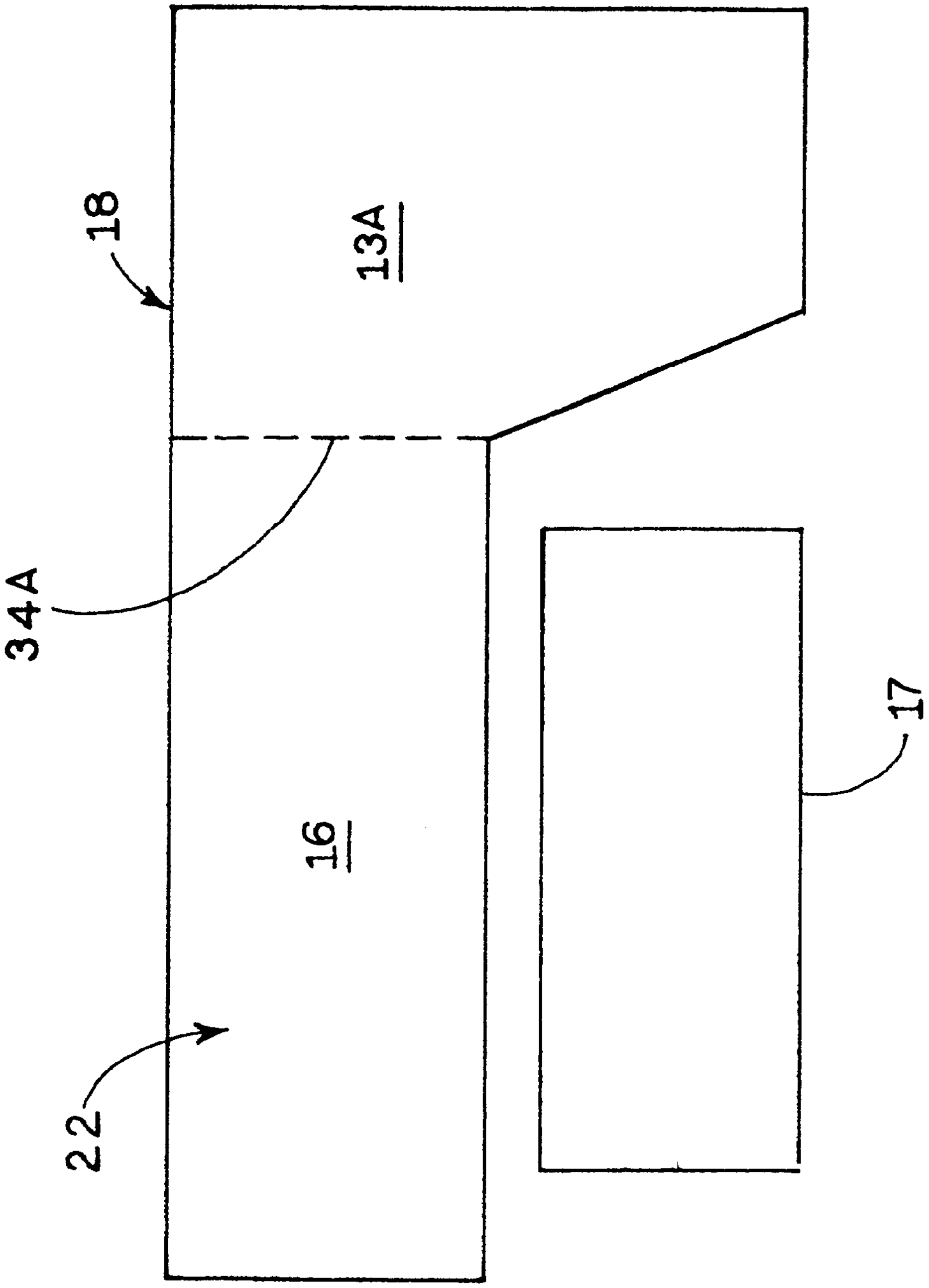
FIG. 6 is a representative top view of a multiple-aviary-unit fourth embodiment, of the bier system of FIG. 4.

The aviary of FIG. 6 is similar to the 3-unit aviary of FIG. 5 with the omission of the unit defining left section 12A. Thus, right section 13A and rear section 16 are defined by separate aviary units joined at opening 34A represented by the illustrated dashed line. As in FIG. 5, the combination of the respective interior chambers of rear section 16 and right section 13A define a unitary composite interior chamber 22, such that birds can fly through the opening 34A between the respective interior chambers.

Figure 7:
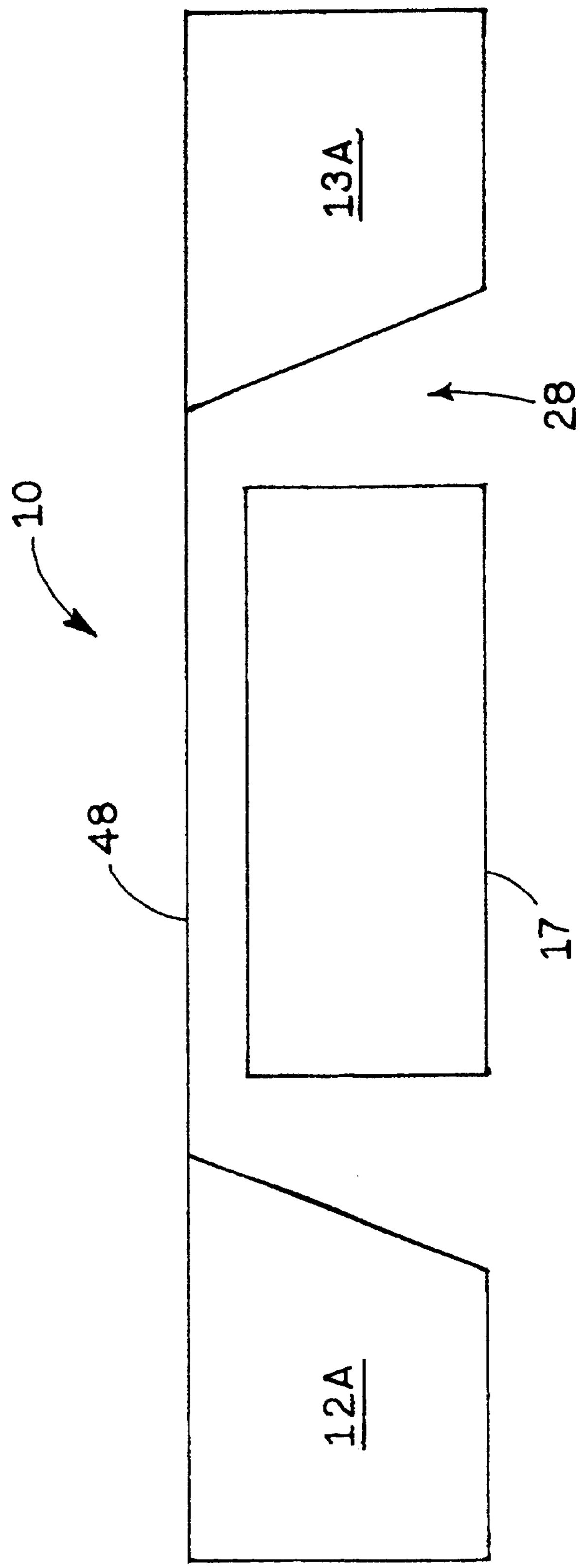
FIG. 7 is a top view of a fifth embodiment of bier systems of the invention.

FIG. 7 illustrates a top view of a fifth embodiment which comprises a bier system 10 having a rear wall 48 connecting the left section 12A to the opposing right section 13A whereby the bier is located within recess 28 and outside the enclosing structure as well as outside the perimeter of the aviary structure, as in above described embodiments. Rear wall 48 comprises a generally two-dimension component not having an enclosing chamber, and thus lacking a volume in which birds can be retained. Rear wall 48 connects sections 12A, 13A, thus maintaining aviary 18 having a unitary and/or "furniture-like" appearance while providing an apparent recess 28 receiving the bier. As suggested by FIG. 7, in this embodiment, the birds are restricted individually to the respective left and right sections 12A, 13A, and have no chamber-to-chamber freedom of movement between the left and right chambers of the respective left and right sections. Namely, the embodiment of FIG. 7 does not comprehend a unitary composite interior chamber 22 such as illustrated in FIGS. 1–6.

Figure 8:
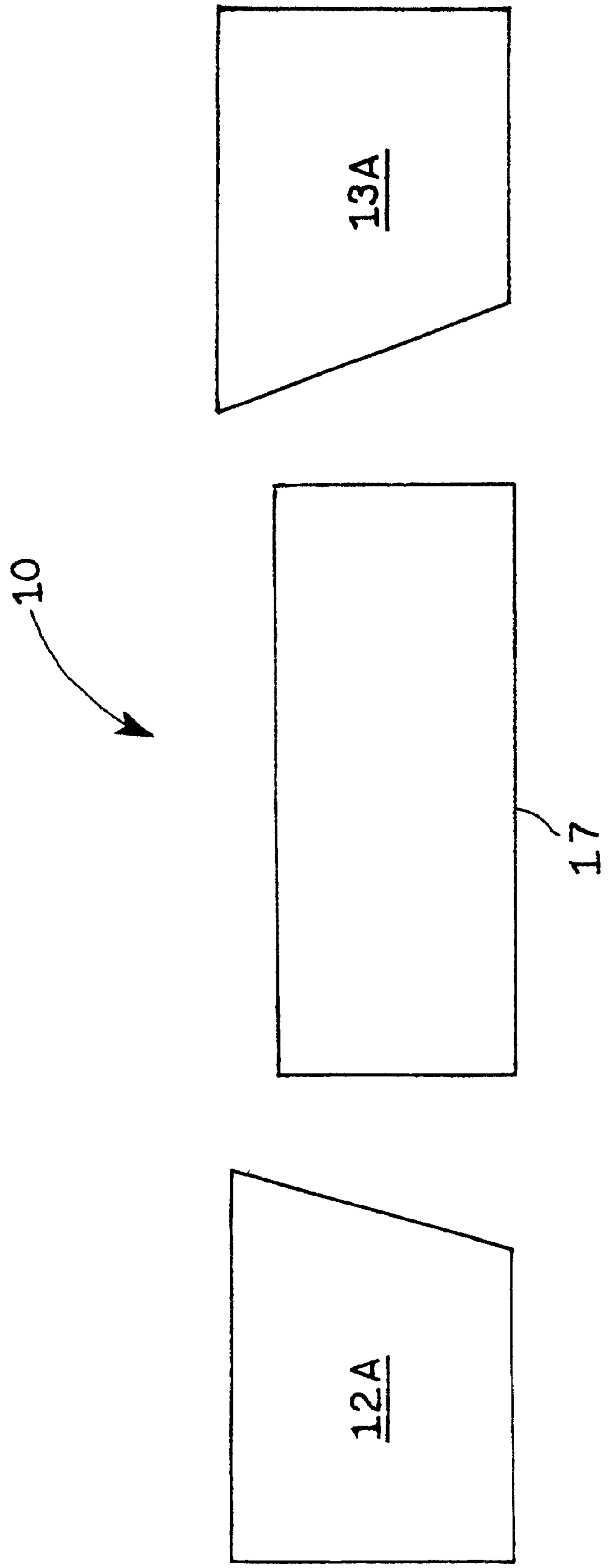
FIG. 8 is a top view of a sixth embodiment of bier systems of the invention, namely with the rear panel removed from the bier system of FIG. 7.

FIG. 8 illustrates left and right sections 12A, 13A of the aviary at opposing ends of bier 17, and wherein rear unit 16 of e.g. FIG. 5, or rear wall 48 of FIG. 7, has been omitted. Such modification obviates the definition of the aviary as a unitary structure, as having a unitary interior composite chamber, and as having a closed outer perimeter. However, the sensory proximity of the aviary sections 12A, 13A to bier 17 maintains common identity among aviary sections 12A, 13A and bier 17. As in the embodiment of FIG. 7, the birds are confined within the respective left and right aviary units.

Figure 9:
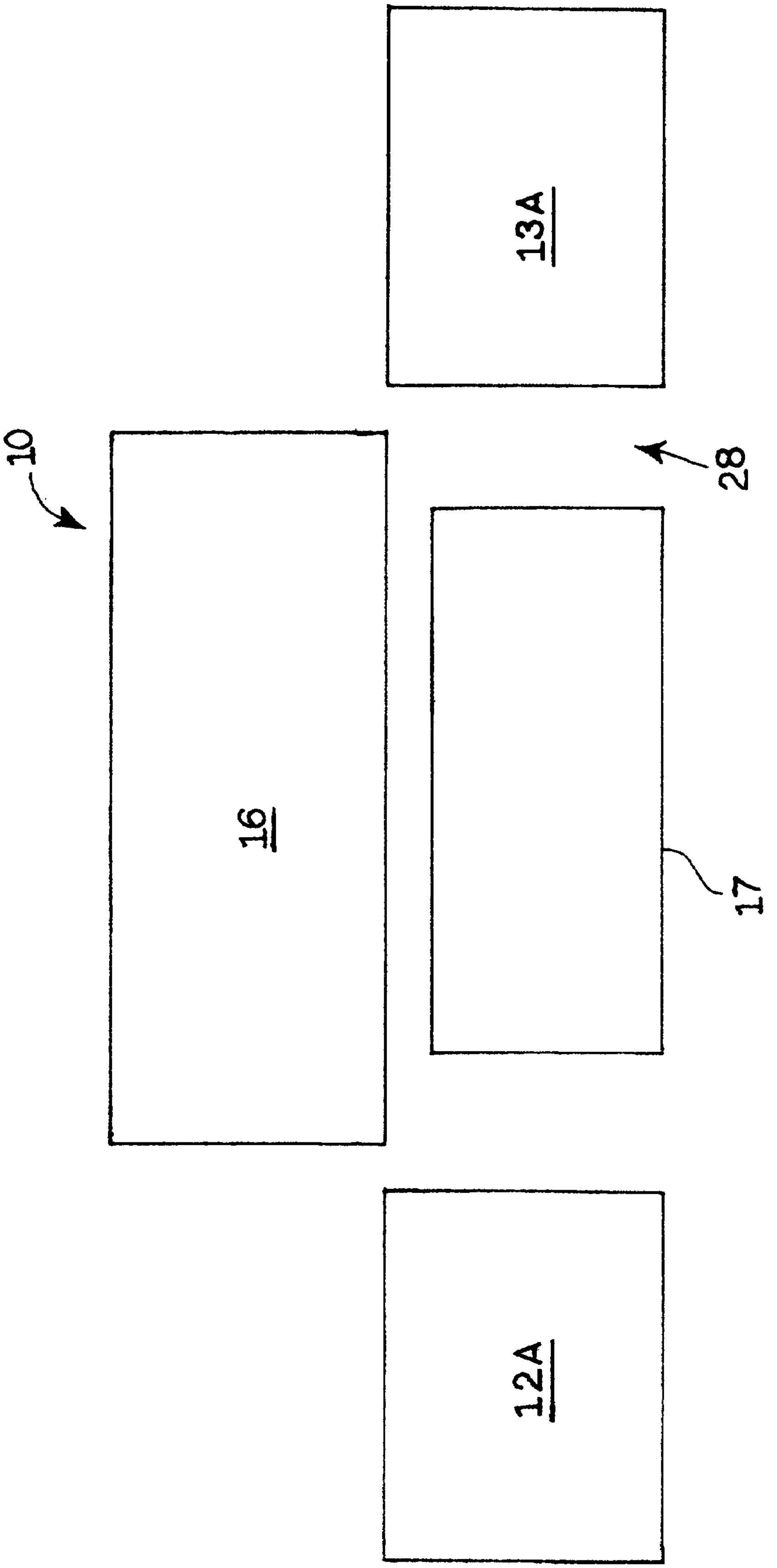
FIG. 9 is a top view of a seventh bier system of the invention, having separate but associated left, right, and rear aviary units.

In a further embodiment, illustrated in FIG. 9, three individual aviary units 12A, 13A, and 16, are juxtaposed on three sides of bier 17, but are not attached to each other or to the bier. While the configuration and layout in FIG. 9 fall short of defining a continuous structural portion of the perimeter of the aviary about recess 28, the close proximity of the units 12A, 13A, 16 to each other provides the effective perception of the existence of recess 28, and the corresponding perception that units 12A, 13A, and 16 provide the same, or similar, "surround" environment for bier 17 as where recess 28 is defined by a continuous structural portion of the perimeter of the aviary. Thus, the perceived sensory proximity of sections 12A, 13A, 16 to each other and to bier 17 provide the effective perception that the aviary sections and the bier, in combination, function as a single bier system. The spacing of the system elements with respect to each other must be such that a person visiting the bier will readily sense the presence of, and any bird activity in, at least one of sections 12A, 13A, 16.

Additional decorative or other appurtenances (not shown) can be used to further develop the perception of units 12A, 13A, 16 providing a "surrounding" environment, defining recess 28 which receives bier 17.

Figure 10:
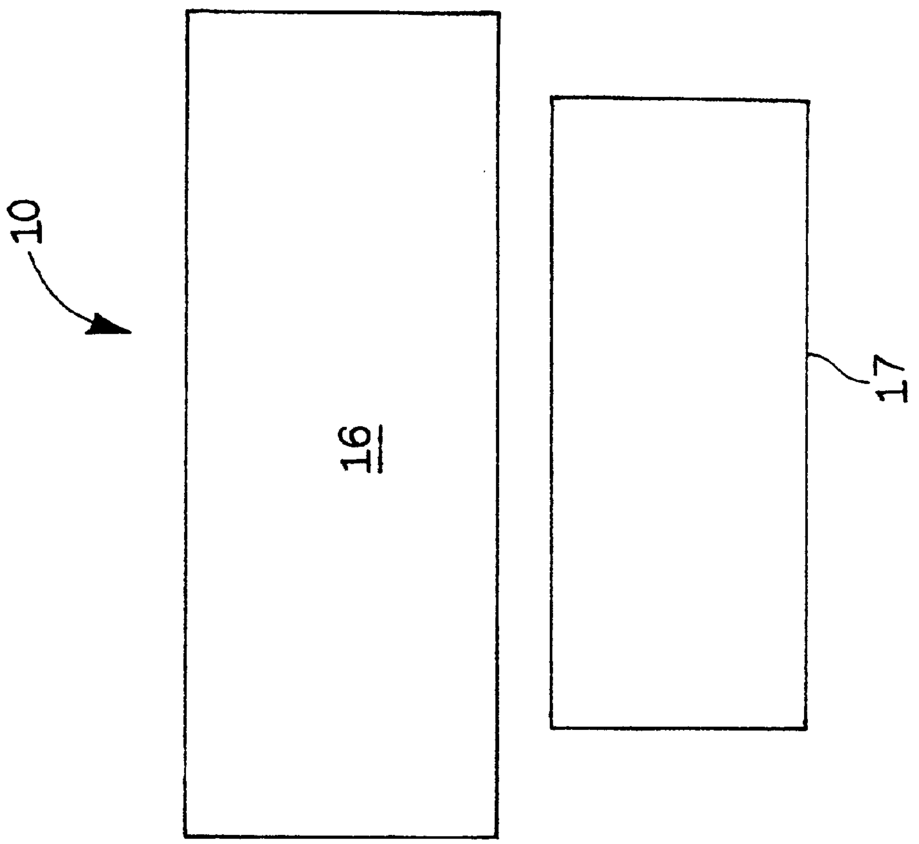
FIG. 10 is a top view of the bier system of FIG. 9, with the side aviary units removed.

Many variations of the embodiment of FIG. 9 are possible. For example, as illustrated in FIG. 10, rear unit 16 can be used alone, or any two or all three of the units 12A, 13A, 16 can be used in various combinations, both in number and location.

Any of the sections 12A, 13A, 16 can be fabricated from multiple segments, as desired. Similarly, any of the aviary units can take on various shapes in addition to rectangular, such as trapezoids (FIG. 8), irregular pentagon (FIG. 5), squares, circles, ovals, and the like. While FIGS. 5 and 8 represent 2-dimensional expressions of such aviaries, all the above shapes can also be expressed in three dimensions, and can thus provide a wide variety of 3-dimensional spaces as the interior chambers of the respective aviaries or aviary sections.

It is contemplated that the operation and functions of the invention have become fully apparent from the foregoing description of elements, but for completeness of disclosure, the usage of the invention will be briefly described.

Aviary 18 is of sufficient size to comprise doors, or other openable structures such as panels, large enough to enable a person to enter into the aviary, or to insert his or her head and/or a major portion of the trunk of his or her body into the interior chamber of the aviary to clean the aviary or to provide any other care to the birds and/or to the aviary.

The aviary is large enough to promote and sustain a high level of activity within the aviary such as flying, landing, perching, feeding young, building nests, and other similar types of bird activity possible within a large environment and some of which is substantially suppressed in a conventional bird cage.

A typical person entering into a funeral home, mausoleum, or other such building, usually approaches the bier. Where the invention is being employed in such building, as the individual so approaches the bier, the activity of the birds becomes sensorily perceptible and begins to penetrate the person's consciousness audibly, visibly, or both. The closer the person approaches the bier system, the greater the potential for sensory perception of the sight and sound of the birds. Hence, as a bereaved person approaches the bier system, the birds are noticeable and generally have a positive emotional effect on the person.

Particularly, the bereaved are generally drawn toward the life, color, and song or chirping, or other movement, sound, or other visible display of the birds. As the bereaved person or other persons view and hear the birds, the pall of death is somewhat replaced by the bird-related atmosphere of light-hearted life. As a result of the uplifting effect of the birds, such persons can more easily recall positive memories of the funeral environment and funeral activities. Further benefits of the bier system include helping the bereaved accept the concept that life continues.

As illustrated hereinbefore, a wide variety of embodiments of the invention can be used to achieve the positive benefits bestowed upon the bereaved by the birds. In all embodiments, the aviary is closely located adjacent, and is definitively associated with, the bier such that the bereaved, while viewing the representation of the deceased on the bier, readily perceive activity of birds located within the aviary.

In the first embodiment, the aviary defines a closed outer perimeter having a recess large enough to receive the bier, and to surround the bier on three sides. At least a portion of the bier is preferably located within the recess at any given moment. The effect of such 3-side-surround embodiment of FIG. 1 is to maximize the uplifting affect of the activity of the birds in the aviary, to thereby provide a high level of encouragement to the bereaved.

Other embodiments allow various modifications to the structure of the bier system to suit the varying needs of the bereaved or other persons using the bier system and/or other requirements of the building structure within which the bier system is located. Such variations, as described in detail above, comprise the rear section in combination with the right section and/or the left section.

Openings can be placed between respective sections to define a unitary composite chamber to allow birds to fly between the interior chambers of the respective sections.

The left section and the right section can be placed at opposing ends of the bier system.

A rear wall can optionally connect the left section to the right section whereby the bier, itself, is located within the recess and outside the enclosing structure as well as outside the perimeter of the aviary structure as in the above described embodiments.

The three sections of the aviary can, in combination, be juxtaposed on three sides of the bier, as three separate but cooperating aviary units, without any of the units necessarily contacting each other, or necessarily joined to each other, or the bier, though such contact and/or joinder are contemplated in some embodiments.

A rear or side section/unit 16 can be used alone, or any two or all three of the sections can be used in various combinations, and can include openings between the sections to construct the type or design of aviary deemed most beneficial to the use contemplated for the aviary.

As used herein, "representation of the deceased" includes such common representations as, for example, and without limitation, the body in an open casket, the body in a closed casket, an empty casket specifically associated with funeral or other after-life activities conducted in remembrance of the deceased, ashes of the deceased left after cremation, and the like.

Having thus described the invention in substantial detail, it will be readily apparent that various changes and modifications may be made without departing from the spirit of the invention. All such changes and modifications are contemplated as being within the scope of the present invention, as defined by the following claims.

To the extent the following claims use means plus function language, it is not meant to include there, or in the instant specification, anything not structurally equivalent to what is shown in the embodiments disclosed in the specification.

Having thus described the invention, what is claimed is:

1. A bier system, comprising:

(a) a bier for receiving a representation of the deceased thereon, said bier having a first length and a first width; and (b) an aviary, said aviary comprising an enclosing aviary structure defining at least one interior chamber for receiving birds therein, said aviary having a second length and a second width, one of the second length and the second width being at least as great as one of the first length and the first width, said aviary being sufficiently small to fit inside a building in which said aviary is to be used in combination with after-life activities, said bier being disposed outside said aviary, said aviary being juxtaposed sufficiently close to said bier that a person approaching said bier makes a definite association of activity of any bird in the aviary with the proximity of the bier.

2. A bier system as in claim 1, said aviary defining a closed outer perimeter, and a recess in the outer perimeter, outside said enclosing aviary structure, at least a portion of said bier being disposed in the recess.

3. A bier system as in claim 2, said bier being disposed entirely within the recess.

4. A bier system as in claim 1, said aviary being sufficiently small in size and weight that said aviary can be moved using furniture-moving equipment.

5. A bier system as in claim 1, said enclosing structure defining a volume of at least 50 cubic feet.

6. A bier system as in claim 1, said enclosing structure defining a volume of at least 65 cubic feet.

7. A bier system as in claim 1, said enclosing structure defining a volume of at least 100 cubic feet.

8. A bier system as in claim 1, comprising a left section and a right section, at left and right respective sides of said bier system, said left section having a first interior chamber and said right section having a second, separately defined interior chamber.

9. A bier system as in claim 8, further comprising a rear wall extending from a rear portion of said left section, behind said bier, to a rear portion of said right section.

10. A bier system as in claim 1, comprising a first rear section, and a second side section, defining respective first and second interior chambers, and further comprising an opening between the first and second interior chambers, whereby the first and second interior chambers define a unitary composite interior chamber.

11. A bier system as in claim 10, the opening between the first and second interior chambers being sufficiently large that birds can fly through the opening, between the first and second interior chambers.

12. A bier system as in claim 10, the interior chambers of said first and second sections in combination defining a volume of at least 50 cubic feet.

13. A bier system as in claim 10, the interior chambers of said first and second sections in combination defining a volume of at least 65 cubic feet.

14. A bier system as in claim 10, the interior chambers of said first and second sections in combination defining a volume of at least 100 cubic feet.

15. A bier system as in claim 10, said aviary defining a closed outer perimeter, and a recess in the outer perimeter, outside said enclosing structure, at least a portion of said bier being disposed in the recess.

16. A bier system as in claim 15, said bier system being disposed entirely within the recess.

17. A bier system as in claim 10, said aviary being of sufficiently small size and weight that said aviary can be moved using furniture-moving equipment.

18. A bier system as in claim 1, comprising a left section, a right section, and a rear section, said left section having a first interior chamber, said right section having a second interior chamber, and said rear section having a third interior chamber.

19. A bier system as in claim 18, further comprising first and second openings between the third interior chamber and the first and second interior chambers, respectively, whereby said first, second and third interior chambers define a unitary composite interior chamber, such that birds can fly through the first and second openings and thus among all of the first, second, and third interior chambers.

20. A bier system as in claim 18, the interior chambers of said first, second, third sections in combination defining a volume of at least 100 cubic feet.

21. A bier system as in claim 18, the interior chambers of said first, second, and third sections in combination defining a volume of about 100 cubic feet up to at least about 150 cubic feet.

22. A bier system as in claim 21, the interior chambers of said first, second, and third sections in combination defining a volume of up to at least about 300 cubic feet.

23. A bier system as in claim 21, the interior chambers of said first, second, and third sections in combination defining a volume of up to at least about 1000 cubic feet.

24. A bier system as in claim 18, the interior chambers of said first, second, and third sections in combination defining a volume of about 100 cubic feet up to at least about 200 cubic feet.

25. A bier system as in claim 18, said aviary defining a closed outer perimeter, and a recess in the outer perimeter, outside said enclosing structure, at least a portion of said bier being disposed in the recess.

26. A bier system as in claim 25, said bier being disposed entirely within the recess.

27. A bier system as in claim 18, said aviary being of sufficiently small size and weight that said aviary can be moved using furniture-moving equipment.

28. A funeral parlor defining at least one room in a building, side walls defining a length and a width of said funeral parlor, a bier system inside said funeral parlor, said bier system comprising a bier for receiving a representation of a deceased thereon, and an aviary defining at least one interior chamber therein, the size of the interior chamber being enabling of free flight of a finch-size bird within the interior chamber, the bier being disposed outside the aviary, the aviary being sufficiently close to the bier that a person approaching the bier makes a definite association of activity of any bird in the aviary with the proximity of the bier.

* * * * *